United States Patent [19]

Suzuki et al.

[11] Patent Number: 4,770,758

[45] Date of Patent: Sep. 13, 1988

[54] AIR/FUEL RATIO DETECTOR

[75] Inventors: Hiroyoshi Suzuki; Seiya Kominami, both of Hyogo, Japan

[73] Assignees: Mitsubishi Denki Kabushiki, Tokyo; NGK Spark Plug Co., Ltd., Nagoya, both of Japan

[21] Appl. No.: 807,180

[22] Filed: Dec. 10, 1985

[30] Foreign Application Priority Data

Dec. 10, 1984 [JP] Japan .................. 59-260130

[51] Int. Cl.⁴ .......................................... G01N 27/56
[52] U.S. Cl. .................. 204/406; 204/407; 204/412; 123/440; 422/94; 422/98
[58] Field of Search .................. 422/62, 83, 94, 98; 204/425, 426, 407, 410, 412, 406; 123/440

[56] References Cited

U.S. PATENT DOCUMENTS

| | | | |
|---|---|---|---|
| 4,272,329 | 6/1981 | Hetrick et al. | 204/426 |
| 4,450,065 | 5/1984 | Yamada et al. | |
| 4,586,476 | 5/1986 | Asayama et al. | 204/426 |
| 4,615,787 | 10/1986 | Yamada et al. | 204/412 |

FOREIGN PATENT DOCUMENTS

| | | |
|---|---|---|
| 0147988 | 7/1985 | European Pat. Off. . |
| 0147989 | 7/1985 | European Pat. Off. . |
| 3445727 | 7/1985 | Fed. Rep. of Germany . |
| 3445755 | 8/1985 | Fed. Rep. of Germany . |
| 3445754 | 8/1985 | Fed. Rep. of Germany . |
| 153155 | 9/1983 | Japan . |

OTHER PUBLICATIONS

Hetrick et al., Oxygen Sensing by Electrochemical Pumping, Mar. 1, 1981, Appl. Phys. Lett., 38(5), pp. 390–392.

Primary Examiner—Benoit Castel
Attorney, Agent, or Firm—Staas & Halsey

[57] ABSTRACT

An air/fuel ratio detector includes an exhaust diffusion chamber having one wall formed by an oxygen pump and another wall formed by an oxygen-concentration difference-actuated electrochemical cell that generates an oxygen differential signal corresponding to the difference in oxygen concentration between exhaust gas in the diffusion chamber and the ambient atmosphere. The differential signal is compared to a reference signal and the difference is used to control a current supplied to the oxygen pump in order to control the oxygen concentration in the exhaust gas. The current level is an indication of the existing air/fuel ratio.

2 Claims, 2 Drawing Sheets

AIR/FUEL RATIO DETECTOR

FIELD OF THE INVENTION

The present invention relates to an air/fuel (A/F) ratio detector, and, more particularly, to an A/F ratio detector that allows an automobile to run at the proper A/F ratio by detecting the A/F ratio of the exhaust gas from an internal combustion engine.

BACKGROUND OF THE INVENTION

An oxygen sensor comprising an oxygen ion-conductive solid electrolyte (e.g. stabilized zirconia) coated with a porous electrode layer (e.g. a platinum porous layer) is known. This sensor detects the theoretical A/F ratio of the exhaust gas from a burning device such as an automotive internal combustion engine in terms of the change in the electromotive force generated by the differential oxygen concentration as between the exhaust gas and the atmosphere. By means of this A/F ratio detection, the sensor will enable the engine to run at the theoretical A/F ratio.

This sensor provides a large difference in output when the A/F ratio, i.e., the weight ratio of air to fuel, is at the theoretical value of 14.7 but produces an insignificant output change when the engine is running in non-theoretical A/F regions. Therefore, the proper A/F ratio control cannot be realized by this sensor except at the theoretical A/F ratio.

Unexamined Published Japanese Patent Application No. 153155/1983 proposes an oxygen sensor using two elements, arranged parallel to each other with a gap therebetween. Each element is composed of a solid electrolyte plate having an electrode layer formed on both sides at the tip. One of the elements is used as an oxygen pump and the other element is used as an oxygen-concentration-difference-actuated electrochemical cell that detects the differential oxygen concentration as between air in the gap and exhaust gas supplied by a pump element.

The sensor disclosed in the referenced application is capable of detecting the A/F ratio of an engine over substantially the full operating range. However, it has been found that because of a V-shaped A/F ratio vs. output profile having minimum output at the theoretical A/F ratio, this sensor detects two values of A/F ratio for the same output and cannot be effectively used for the purpose of A/F ratio control unless it is definitely known whether the engine is operating in the fuel-rich or fuel-lean region.

OBJECTS AND SUMMARY OF THE INVENTION

An object of the present invention is an air/fuel ratio detector that provides an accurate output over the fuel operating range of an engine.

Another object of the present invention is an air/fuel ratio detector for use in the accurate control of the air/fuel mixture supplied to an engine.

Still a further object of the present invention is an air/fuel detector that is valuable and may be economically produced.

These and other objects are attained by an air/fuel ratio detector comprising a diffusion compartment having a first wall and a second wall and being adapted to be supplied with exhaust gas, an oxygen pump forming the first wall of the diffusion compartment, means for supplying a pump current to the oxygen pump to pump oxygen ions from the diffusion compartment, an oxygen-concentration differential sensor having a first surface forming the second wall of the diffusion compartment and a second surface in contact with the ambient atmosphere, the sensor for producing a differential signal having a value corresponding to the difference in ion concentration between the diffusion compartment and the ambient atmosphere, current control means for controlling the supplying means to provide a selected current to the oxygen pump, means for comparing the differential signal to a reference signal corresponding to the difference in oxygen concentration between exhaust gas and ambient atmosphere at a preferred air/fuel ratio and for controlling the current control means to supply a current to the oxygen pump to cause the oxygen pump to establish an oxygen concentration in the diffusion compartment such that the difference signal and the reference signal are equal, and means for indicating the air/fuel ratio from the level of the pump current supplied by the supplying means.

BRIEF DESCRIPTION OF THE DRAWINGS

The manner by which the above objects and other objects, features, and advantages of the present invention are obtained will become more apparent upon the consideration of the following detailed description in view of the drawings, wherein.

DETAILED DESCRIPTION OF THE PREFERRED EMBODIMENTS

Figure 1:
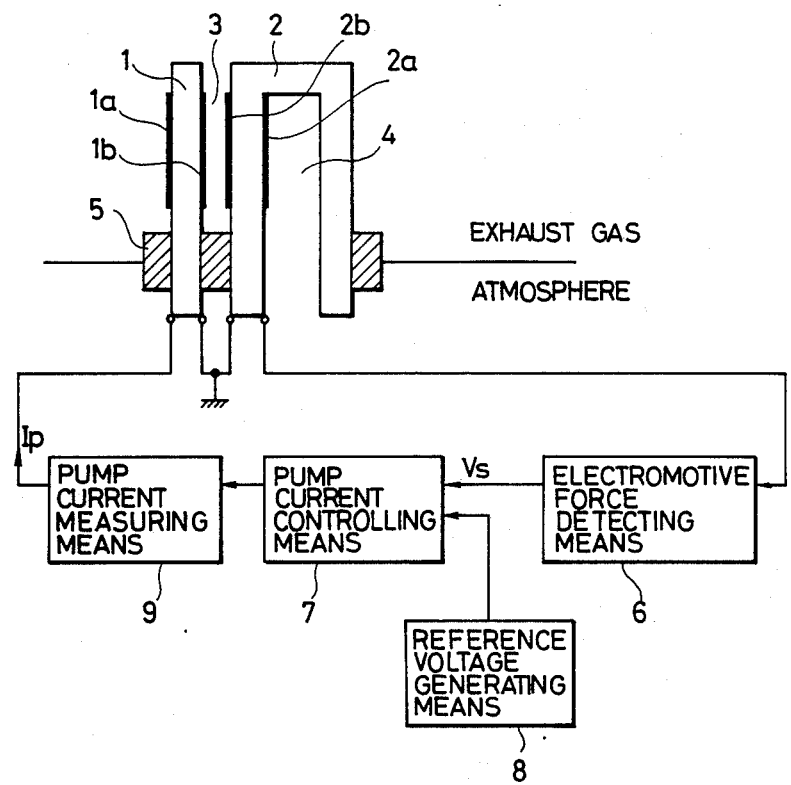
FIG. 1 is a schematic diagram of an air/fuel ratio detector according to the present invention.

FIG. 1 shows the general layout of the A/F ratio detector of the present invention. An oxygen pump unit 1 comprises an oxygen ion-conductive solid electrolyte plate about 0.5 mm thick which has a pair of porous electrodes 1a and 1b formed thereon. An oxygen-concentration-difference-actuated electrochemical cell unit 2 includes an oxygen ion-conductive solid electrolyte plate about 0.5 mm thick which has a pair of porous electrodes 2a and 2b formed thereon. A diffusion compartment 3 permits a limited inflow of exhaust gas and is formed as a slit of a small width in the embodiment shown. An air compartment 4 communicates with the atmosphere and a supporting partition wall 5 supports the oxygen pump unit 1 and the electrochemical cell unit 2 while separating the exhaust gas from the atmosphere.

The electrode 1b on the oxygen pump unit 1 and the electrode 2b on the cell unit 2 are exposed to the diffusion compartment 3. The electrode 1a on the pump unit 1 is exposed to the ambient exhaust gas atmosphere and the electrode 2a on the cell unit 2 is exposed to the air compartment 4 communicating with the atmosphere.

The electrodes 1b and 2b are interconnected before they are grounded in the outside of the detector. FIG. 1 further includes means 6 for detecting the electromotive force Vs generated by the electrochemical cell unit 2, means 7 for controlling the pump current so that the electromotive force Vs is equal to a predetermined reference voltage $V_{REF}$, means 8 for generating the reference voltage $V_{REF}$, and means 9 for measuring the pump current Ip flowing into the pump unit 1.

With the arrangement shown above, the differential oxygen concentration between the diffusion compartment 3 and the air compartment 4 generates an electromotive force Vs in the electrochemical cell unit 2. The electrode 2a that is exposed to the air compartment 4 functions as a positive electrode. The value of Vs is determined by the well known Nernst's equation.

When a pump current Ip is caused to flow through the pump unit 1 from the electrode 1a to 1b, oxygen is pumped as oxygen ions out of the diffusion compartment 3 from the electrode 1b to the electrode 1a. As a result, the oxygen partial pressure in the diffusion compartment 3 decreases to cause an increase in the electromotive force Vs generated by the cell unit 2. The electromotive force Vs is detected by the detecting means 6 and compared with the reference voltage $V_{REF}$. If $Vs < V_{REF}$, the pump current Ip is increased to pump a greater amount of oxygen from the diffusion compartment 3 so that the electromotive force Vs is increased. If $Vs > V_{REF}$, the pump curent Ip is decreased to pump a smaller amount of oxygen from the diffusion compartment 3 so that Vs is decreased. In this manner, the pump current Ip is controlled so that Vs is always equal to $V_{REF}$. The pump current Ip so controlled is measured by the measuring means 9 and delivered from the detector either as a current or voltage output.

Figure 2:
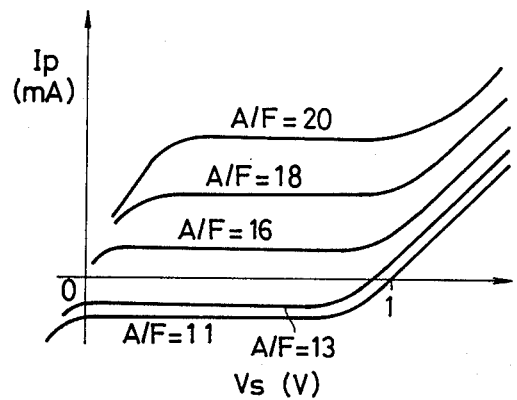
FIG. 2 is a characteristic diagram plotting the pump current Ip vis-a-vis the electromotive force Vs for various levels of the air/fuel ratio.

FIG. 2 is the characteristic diagram obtained by running a 2,000-cc gasoline engine for a Japanese passenger car equipped with the A/F ratio detector having the arrangement shown in FIG. 1. In the experiment, the A/F ratio of the air/fuel mixture supplied to the engine was varied stepwise from 11 to 20, and the pump current Ip flowing through the pump unit 1 was measured for varying values of the reference voltage $V_{REF}$, or the electromotive force Vs of the cell unit 2.

In obtaining the data shown in FIG. 2, the direction of the pump current Ip was reversed in the fuel-rich region where the A/F ratio was less than the theoretical 14.7 and in the region where Vs was less than about one volt. The flat portion in FIG. 2, i.e., where Ip remained constant irrespective of the change in Vs, indicate that the oxygen partial pressure in the diffusion compartment 3 became substantially equal to the value for the theoretical A/F ratio.

Figure 3:
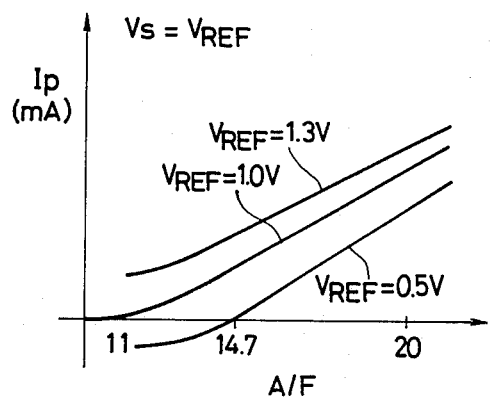
FIG. 3 is a characteristic diagram plotting the air/fuel ratio against the pump current, Ip, for three different values of reference voltage, $V_{REF}$.

FIG. 3 is an output characteristic diagram obtained by plotting the pump current Ip against the A/F ratio, with the reference voltage $V_{REF}$ (i.e., Vs in FIG. 2) being taken as a parameter and selected at 0.5 V, 1.0 V and 1.3 V. When the reference voltage $V_{REF}$ was held to be no more than about 0.8-1.0 volt, which was the electromotive force generated by the differential oxygen concentration as between the atmosphere and the exhaust gas at the theoretical A/F ratio, the direction of the pump current Ip had to be reversed in order to detect values of A/F ratio lower than the theoretical 14.7. This requires the use of complicated electrical circuitry for the pump current control means 7 and pump current measuring means 9, as typified by the need for using a reversible power supply for the pump current control circuit.

On the other hand, when the reference voltage $V_{REF}$ was held at a predetermined value (1.0 V or 1.3 V in the embodiment shown) equal to or higher than the electromotive force generated by the differential oxygen concentration as between the atmosphere and the exhaust gas at the theoretical A/F ratio, a positive Ip vs. A/F ratio characteristic was obtained where Ip increased steadily with increasing A/F ratio over the full range of the practical possible values of A/F ratio. This linear relationship enables the use of a simple electrical circuit for operating the pump current control means and the pump current measuring means. At the same time, by employing the output of the detector, feedback control for attaining the desired A/F ratio can be readily implemented irrespective of whether the engine is operating in the fuel-rich or fuel-lean region.

The foregoing description of the present invention assumes that it is used as an A/F ratio detector with an automotive internal combustion engine, but it should be understood that the invention may also be employed as an A/F ratio detector for other internal combustion engines and burning devices.

As will be apparent from the foregoing description, the sensor of the present invention comprises an oxygen pump unit and an oxygen-concentration-difference-actuated electrochemical cell unit. The pump unit is formed of an oxygen ion-conductive solid electrolyte and is partly exposed to a diffusion compartment that will permit a limited inflow of the exhaust gas and from which oxygen will be discharged. The electrochemical cell unit is also made of an oxygen ion-conductive solid electrolyte and is formed between said diffusion compartment and the atmosphere or an air compartment communicating with the atmosphere. In accordance with the present invention, the pump current flowing through the oxygen pump unit is so controlled that the electromotive force generated by the electrochemical cell unit will be held at a predetermined voltage which is not smaller than the electromotive force obtained by a the differential oxygen concentration as between the exhaust gas at the theoretical air/fuel ratio and the atmosphere. By means of measuring the so controlled pump current, a characteristic is provided where the pump current is positive and increases steadily with the A/F ratio over the range conceivably possible for practical purposes. Because of this linear characteristic, the detector of the present invention permits the use of simplified electrical circuits for the pump current control means and the pump current measuring means and, hence, can be manufactured at a fairly low cost. The pump current characteristic described above has another advantage in that it enables the A/F ratio to be easily controlled at the desired value irrespective of whether the engine is operating in the fuel-rich or fuel-lean region.

What is claimed is:

1. An air/fuel ratio detector, comprising:
a diffusion compartment having a first wall and a second wall and being adapted to be supplied restrictively with exhaust gas;
an air compartment having a wall and communicating with ambient atmosphere;
a solid electrolytic plate-like oxygen pump forming said first wall of said diffusion compartment, said oxygen pump comprising a first oxygen ion-conductive solid electrolyte plate having a first porous electrode formed on one surface thereof and a second porous electrode formed on the opposite surface thereof, said opposite surface of said first plate forming said first wall of said diffusion compartment;
means for supplying a pump current with a direction to said oxygen pump so as to pump out oxygen from said diffusion compartment;

a solid electrolytic plate-like oxygen-concentration differential sensor, having a first surface forming said second wall of said diffusion compartment and a second surface forming said wall of said air compartment so as to be in contact with the ambient atmosphere as a constant oxygen content reference gas, for producing a differential signal having a value corresponding to the difference in oxygen concentration between said diffusion compartment and the ambient atmosphere, said oxygen-concentration differential sensor comprising a second oxygen ion-conductive solid electrolyte plate having a third porous electrode formed on said first surface thereof and a fourth porous electrode formed on said second surface thereof;

current control means for controlling said supplying means to provide a selected current to said oxygen pump;

means for comparing said differential signal to a reference signal which is equal to said differential signal having a value corresponding to the difference in oxygen concentration between an exhaust gas at a preferred air/fuel ratio and the ambient atmosphere and for controlling said current control means to supply a current to said oxygen pump to cause said oxygen pump to establish an oxygen concentration in said diffusion compartment such that said differential signal and said reference signal are equal; and means for indicating the air/fuel ratio from the level of said pump current supplied by said supplying means.

2. An air/fuel ratio detector according to claim 1, wherein said differential signal is a voltage signal and said means for comparing includes means for providing said oxygen reference signal having a magnitude equal to or greater than 1 volt.

* * * * *

UNITED STATES PATENT AND TRADEMARK OFFICE
CERTIFICATE OF CORRECTION

PATENT NO. : 4,770,758
DATED : September 13, 1988
INVENTOR(S) : Suzuki et al

It is certified that error appears in the above-identified patent and that said Letters Patent is hereby corrected as shown below:

Title page (73) Assignees: after "Kabushiki" insert
--Kaisha--.
Column 4, line 34, delete "a".

Signed and Sealed this

Eleventh Day of April, 1989

Attest:

DONALD J. QUIGG

*Attesting Officer*

*Commissioner of Patents and Trademarks*